United States Patent [19]

Marelli

[11] Patent Number: 5,174,473
[45] Date of Patent: Dec. 29, 1992

[54] DOSE COUNTING DEVICE FOR A DISTRIBUTOR OF DOSES OF FLUID PRODUCTS, ESPECIALLY FOR PHARMACEUTICAL USE

[75] Inventor: Andrea Marelli, Rozzano, Italy

[73] Assignee: Elettro Plastica, S.p.A., Rozzano, Italy

[21] Appl. No.: 727,661

[22] Filed: Jul. 9, 1991

[30] Foreign Application Priority Data

Oct. 9, 1990 [IT]  Italy ................................ 21685 A/90

[51] Int. Cl.⁵ .............................................. B67D 5/22
[52] U.S. Cl. ........................................ 222/38; 222/36;
235/94 R; 116/284; 221/7
[58] Field of Search ....................... 222/36, 38; 221/7;
235/94 R; 116/284, 309, 311

[56] References Cited

U.S. PATENT DOCUMENTS 3,119,557  1/1964  Chapman ........................ 222/36 X
4,188,984  2/1980  Lyall .............................. 222/38 X
4,565,302  1/1986  Pfeiffer et al. ..................... 222/38

FOREIGN PATENT DOCUMENTS 301615   2/1989  European Pat. Off. .
2450640  10/1980  France .
1317315  5/1973  United Kingdom .

Primary Examiner—Andres Kashnikow
Assistant Examiner—Lesley D. Morris
Attorney, Agent, or Firm—Shlesinger Fitzsimmons & Shlesinger

[57] ABSTRACT

The device comprises a distributor provided with an operating member for a counting device of doses of fluid associated with a mouth of a container, a ring nut for fastening the distitributor onto the mouth and resilient element suitable for transforming the translatory motion of said operating member with respect to the ring nut in a rotatory and axially reciprocating motion of a rotating and axially translatable element to cause the appearance of a different numerical index provided on the rotating element at an observation position obtained in the control member.

4 Claims, 3 Drawing Sheets

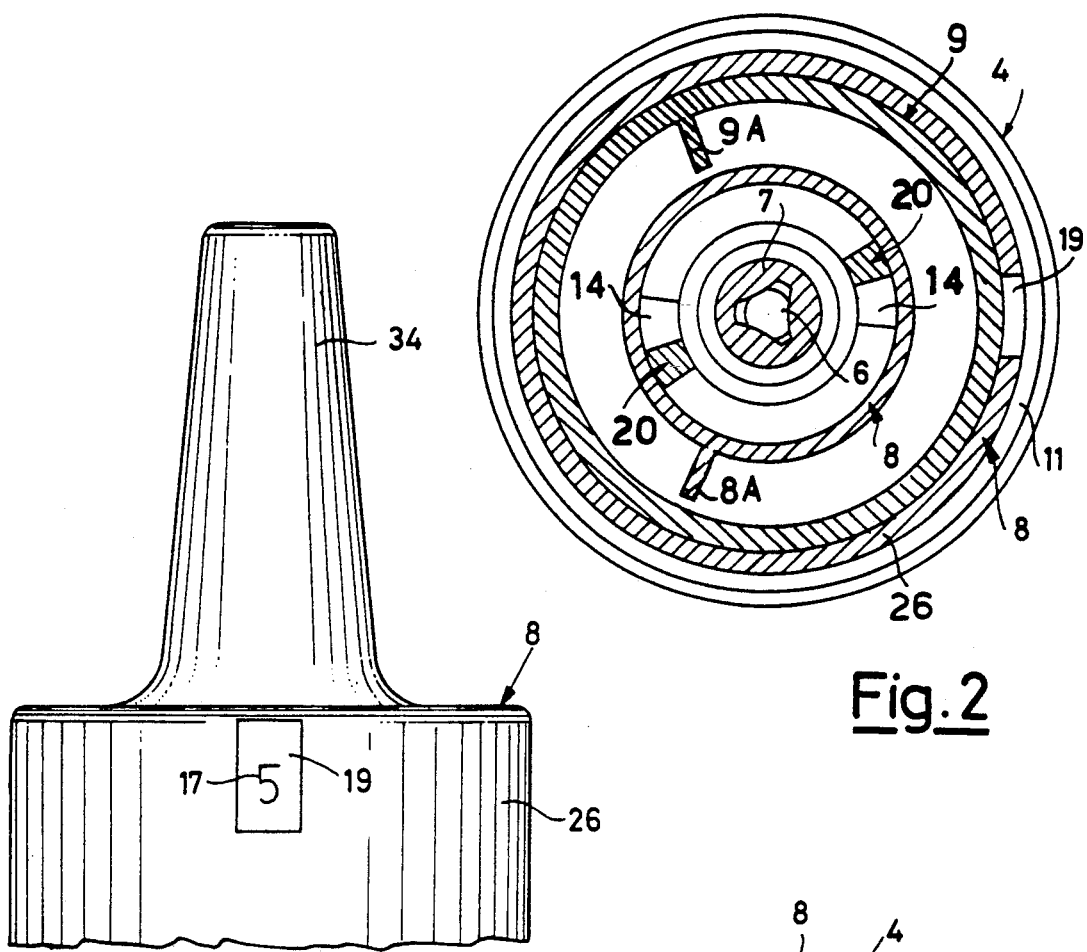
Fig. 2
Fig. 3
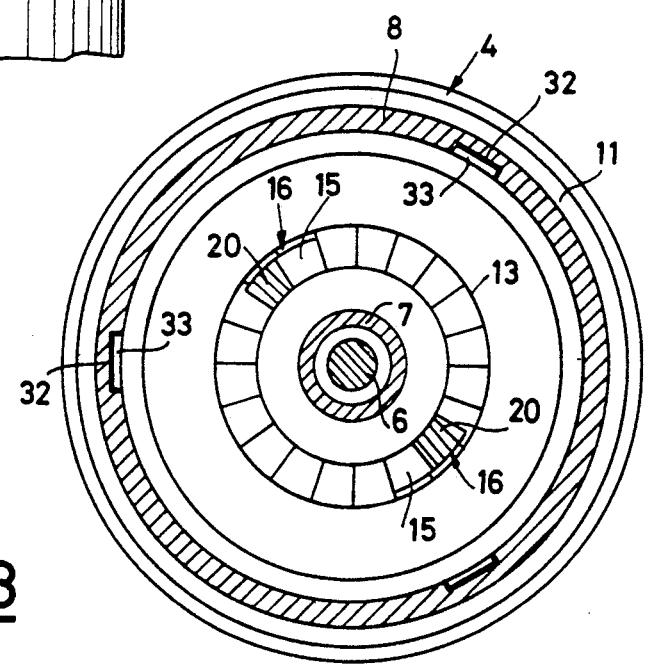
Fig. 6

DOSE COUNTING DEVICE FOR A DISTRIBUTOR OF DOSES OF FLUID PRODUCTS, ESPECIALLY FOR PHARMACEUTICAL USE

DESCRIPTION

The present invention relates to a dose counting device for a distributor of doses of fluid products, especially for pharmaceutical use.

Such dose counting devices find particular application in the field of nasal distributors.

The latter essentially comprise a bottle open at its upper end and tapered for the introduction of a member for the distribution of the product contained inside it. The member for the distribution of the product has a terminal spout at its upper end from which the distributed product is introduced in a truncated-cone element, called <<nasal>>, shaped so as to be able to be inserted in the nasal cavities and thus allow the product to be injected into the nostrils.

A ring nut screwed or fastened to the bottle accomplishes the connection between the bottle, the distribution member and the nasal.

In such distributors the distribution of the product is operated by successive strokes on the nasal so as to cause it to slide with respect to the coupling ring nut and to correspondingly activate the distribution member.

Every stroke imparted to the nasal causes the distribution of a given dose of product. Since the product contained in the nasal distributors consists mainly of substances to be administered in a controlled dose, it is particularly important to have available a dose counting device suitable for visualizing the total number of doses distributed.

The object of the present invention is to accomplish a dose counting device that is easy and safe to use as the distributor of doses of liquid products, especially but not exclusively for nasal distributors, with the possibility of indicating with a progressive numerical index the number of doses distributed over time.

According to the present invention such object is attained with a dose counting device for a dose distributor of fluid products, especially for pharmaceutical use, said distributor comprising a container of liquid product provided with a mouth, means for the distribution of doses of fluid from said container through said mouth, a ring nut for fastening said distributor means onto said mouth of the container, a translatable operating member for the operation of said distribution means, characterized in that it comprises elastic means suitable for transforming the translatory motion of said operating member with respect to the ring nut in a rotatory and axially reciprocating motion of a rotating and axially translatable element provided with progressive numerical indices which can be positioned in succession with every dose distributed in a pre-set observation position, said elastic means comprising a succession of small flexible circumferentially distanced legs having an upper part suitable for reacting with a first set of one-directional teeth of the operating member, a lower part suitable for reacting with a second set of one-directional teeth of the ring nut and an intermediate part fastened to the rotating element, so that when said first set of one-directional teeth approaches said second set of one-directional teeth under the action of said operating member, the upper part of said small legs disengages from the corresponding tooth of the first set of teeth to be inserted in an immediately adjacent tooth and thus drives in rotation and axial forward movement said intermediate part of the small leg and when said first set of teeth is moved away from said second set of teeth when the action of said operating member ceases the lower part of said small legs disengages from the corresponding tooth of the second set of teeth to be inserted in an immediately adjacent tooth and thus drives in rotation and axial backward movement said intermediate part (20) of the small leg (16).

In particular the ring nut is provided with radial ridges suitable for their engagement in slots of the operating member in order to guide the latter's translation with respect to it.

The same dose counter, used in the case in question in the pharmaceutical field, can also find application in cosmetics when fluid products are to be distributed.

There is also the possibility of applying it to a distributor of pills with a controlled dosing.

Given the reduced dimensions wherein it is necessary to silk-screen the numerical indices there is lastly the possiblity of using suitable colour hues for them giving an auxiliary and immediately understandable piece of information.

The features of the present invention shall be made more evident by an embodiment illustrated as a non-limiting example in the enclosed drawings, wherein:

FIG. 2 is a transversal cross-sectional view taken along the line II—II of FIG. 1;

FIG. 3 is a transversal cross-sectional view taken along the line III—III of FIG. 1;

FIG. 6 shows the upper part of the nasal, seen from the right hand side with respect to FIG. 1.

Figure 1:
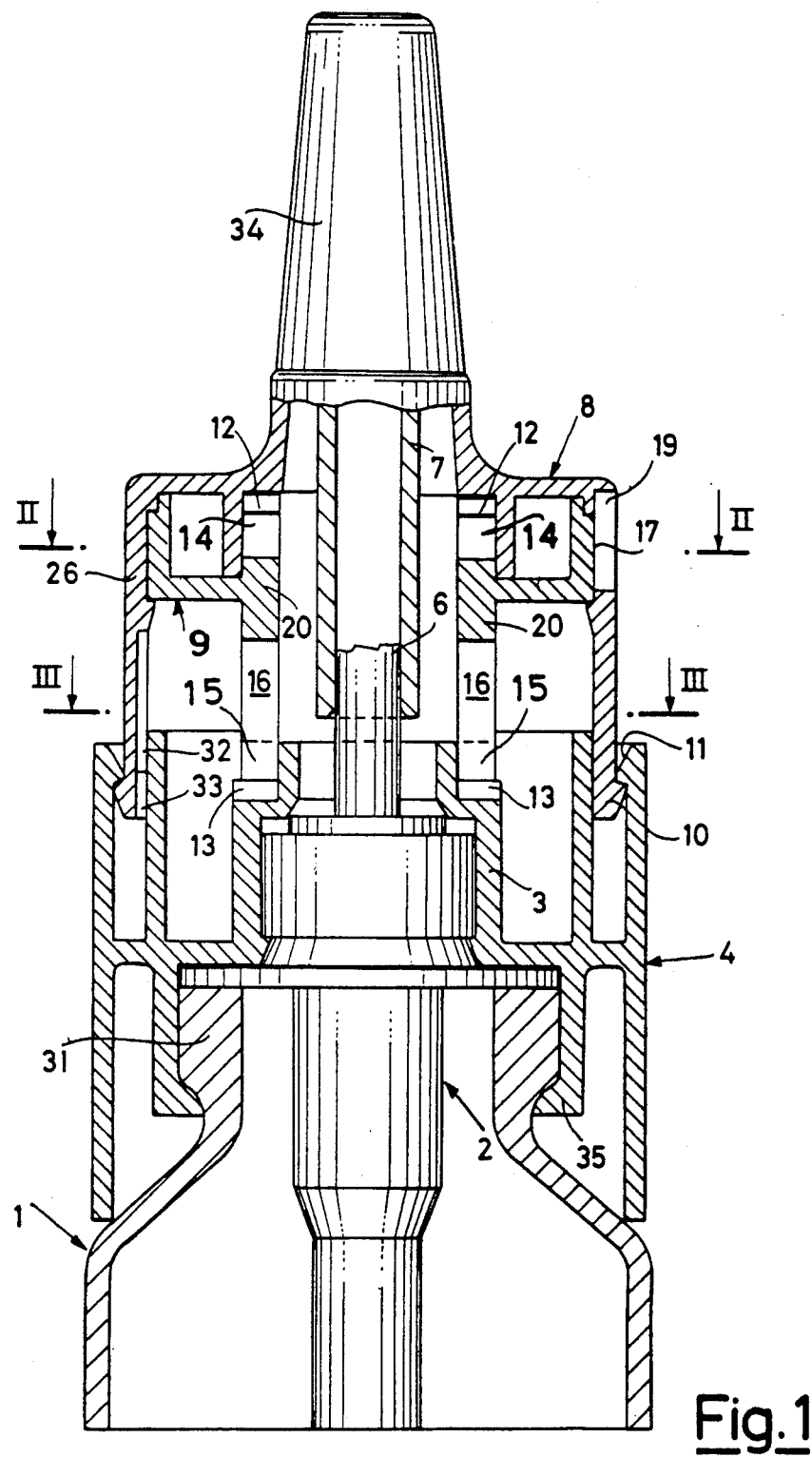
FIG. 1 shows an axial sectional view of a dose counting device according to the present invention.

With reference to FIGS. 1 to 3 and 6, the device comprises a container 1 of a fluid product, not shown, in the form of a bottle with its upper mouth open 31 to allow the introduction inside it of a distribution valve 2 for the fluid contained in it. Such valve 2, already described in the Italian patent application No. 22133 B/87 filed on Jul. 30, 1987 in the name of the same applicant, is associated with the container 1 through a flange 3 forming part of a ring nut 4 fastened to the container 1 by means of an annular protrusion 35 of the same and terminates at the upper end with an axially slidable distribution spout 6 inserted and blocked in a guide channel 7 for the fluid, which forms part of and passes right through an axially translatable nasal 8, constituting the operating member of the valve 2.

The latter is an internally hollow cylinder 26 terminating at its lower end with an annular edge 10 turned outward, connected to a corresponding annular edge 11 of the ring nut 4 so as to prevent the separation of the nasal 8 from the ring nut 4 and provided with axial slots 32 in which there are slidably inserted radial ridges 33 of the ring nut 4 for the axial translation of the nasal 8 with respect to it. At its upper end and in its middle portion the nasal 8 extends in a protrusion 34 shaped in the form of a nose so that it can be inserted into the nostrils for the introduction of the fluid product to be distributed.

Inside both the nasal 8 and the ring nut 4 there are accomplished internal sets of saw-tooth shaped teeth 12, 13 in engagement with corresponding upper parts 14 and lower parts 15 of a circumferential succession of small elastically flexible legs 16 whose intermediate part 20 is integral with a rotating element 9 with progressive numerical indices 17. With reference to FIG. 6, such indices 17 during the rotation of the rotating element 9 are positioned in succession in an observation position constituted by a window 19 obtained in the annular part 26 of the nasal 8, indicating the number of strokes that have been imparted to the nasal 8 up to that time. The rotating element 9 is also provided with a radial locator 9A suitable for coming to a stop against a corresponding locator 8A protruding radially from the nasal 8 to prevent the rotation of the rotating element 9 after a given number of strokes has been imparted to the nasal 8 and thus a pre-set maximum number of doses distributed highlighted, as explained above, by the progressive numerical indices 17 in the window 19.

It should also be noted that in the specific case the ring nut 4 is fastened onto the container 1, but it also possible for the ring nut 4 to be screwed down onto the container 1 itself.

The operation of the dose counting device according to the present invention is as follows.

Figure 4:
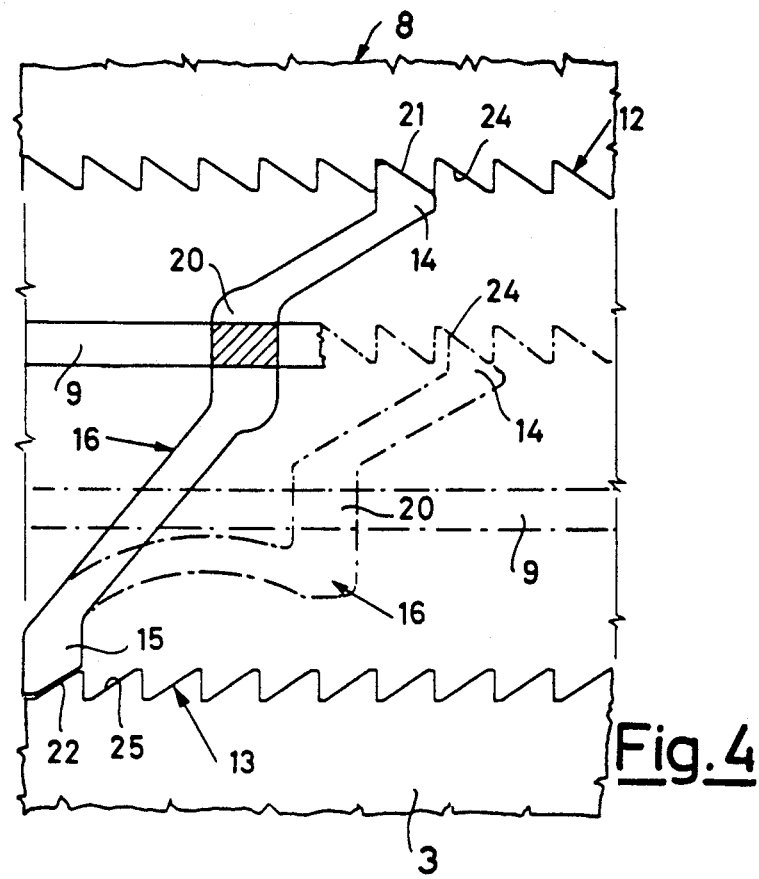
FIG. 4 illustrates with a full line a small flexible leg and the two sets of teeth in the starting position and in a dotted line the same small leg and the corresponding sets of teeth during the course of the operation of the operating member for the distribution of a dose of product.
Figure 5:
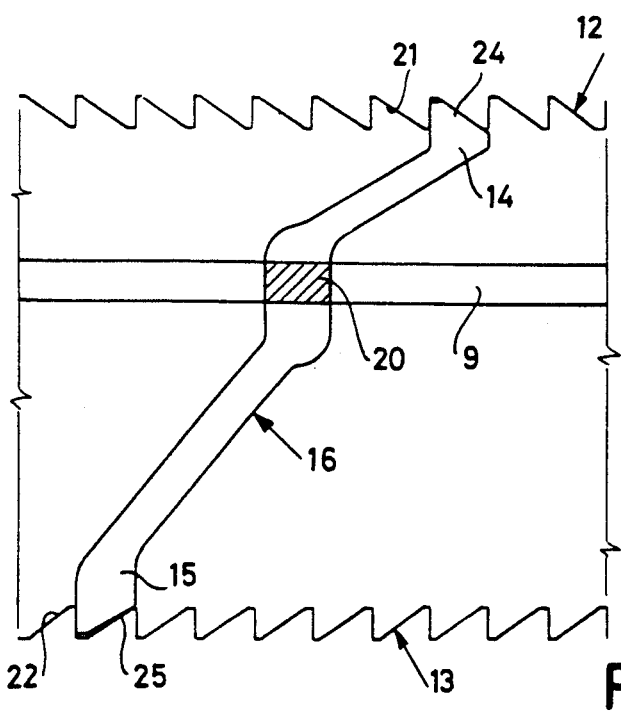
FIG. 5 illustrates the same small leg of FIG. 4 after the return of the operating member to the starting position.

At each operation of the distributor the nasal 8 is moved in an axial translation with respect to the ring nut 4 by the axial depression of the same and thanks to the engagement of the radial ridges 33 of the ring nut 4 in the slots 32 of the nasal 8. More accurately, with reference to FIG. 4, initially the small generic leg 16 of the succession of the small circumferentially distanced legs is with its upper part 14 engaged with a tooth 21 of the internal set of teeth 12 of the nasal 8. The same small leg 16 is now with one of its lower parts 15 engaged with a tooth 22 of the internal set of teeth 13 of the ring nut 4, while its middle portion 20 is integral with the rotating element 9. Pressing on the nasal 8, while the same nasal operates through the slidable spout 6 the valve 2 for the distribution of a dose of product, the small leg 16 is elastically urged by the approach of the set of teeth 12 towards the set of teeth 13 in the configuration illustrated by a dotted line in the same FIG. 4. During this urging its upper part 14 leaves the tooth 21 to position itself in a tooth 24 adjacent to it. With reference to FIG. 5, when the pressure on the nasal 8 is released, the latter translates in a direction opposite to the ring nut 4, the set of teeth 12 moves away from the set of teeth 13 and the lower part 15 of the small leg 16 leaves the tooth 22 to position itself in the tooth adjacent to it. The displacement of the upper part 14 in the notch 24 and of the lower part 15 in the notch 25 is equivalent to the forward movement of the small leg 16 through one position. During this forward movement the intermediate part 20 of the small leg 16 takes with it the rotating element 9 in a unitary rotation. The numerical index 17 attached to the rotating element 9 shall be rotated through one position and behind the window 19 there shall appear the immediately successive numerical index 17, updating the information related to the number of strokes imparted to the nasal 8 and thus to the number of doses distributed. At the end of a given maximum number of strokes imparted to the nasal 8 and thus of a given maximum number of doses of product distributed, the radial locator 9A protruding from the rotating element 9 comes to a stop against the radial locator 8A protruding from the nasal 8. The rotation of the rotating element 9 is blocked and behind the window 19 there appears the progressive numerical index 17 corresponding to the maximum allowed number of doses distributed. Even after the blocking of the rotation of the rotating element 9 it is still possible to press against the nasal 8 in order to use up completely the product contained in the container.

I claim:

1. Dose counting device for a distributor of doses of fluid products, especially for pharmaceutical use, said distributor comprising a container of liquid product provided with a mouth, means for the distribution of doses of fluid from said container through said mouth, a ring nut for fastening said distributor means onto said mouth of the container, a translatable operating member for the operation of said distribution means, characterized in that it comprises elastic means suitable for transforming the translatory motion of said operating member with respect to the ring nut in a rotatory and axially reciprocating motion of a rotating and axially translatable element provided with progressive numerical indices which can be positioned in succession with every dose distributed in a pre-set observation position, said elastic means comprising a succession of small flexible circumferentially distanced legs having an upper part suitable for reacting with a first set of one-directional teeth of the operating member, a lower part suitable for reacting with a second set of one-directional teeth of the ring nut and an intermediate part fastened to the rotating element, so that when said first set of one-directional teeth approaches said second set of one-directional teeth under the action of said operating member, the upper part of said small legs disengages from the corresponding tooth of the first set of teeth to be inserted in an immediately adjacent tooth and thus drives in rotation and axial forward movement said intermediate part of the small leg and when said first set of teeth is moved away from said second set of teeth when the action of said operating member ceases the lower part of said small legs disengages from the corresponding tooth of the second set of teeth, to be inserted in an immediately adjacent tooth and thus drives in rotation and axial backward movement said intermediate part of the small leg.

2. Device according to claim 1, characterised in that said ring nut is provided with radial ridges suitable for their engagement in longitudinal slots of the operating member in order to guide the latter's translation with respect to it.

3. Device according to claim 1, characterised in that said operating member has a top portion in the shape of a nasal.

4. Device according to claim 1, characterised in that said rotating element is provided with a radial locator suitable for coming to a stop against a corresponding radial locator of the operating member to prevent the rotation of the rotating element, but allowing its axial translation, after a given number of strokes has been imparted to the operating member and thus after a given maximum number of doses distributed.

* * * * *